United States Patent
Pomrink et al.

(10) Patent No.: US 9,199,006 B2
(45) Date of Patent: *Dec. 1, 2015

(54) COMBINATION PRODUCTS INCLUDING BIOACTIVE GLASS AND COLLAGEN AND KITS INCLUDING THE SAME

(71) Applicant: NovaBone Products, LLC, Alachua, FL (US)

(72) Inventors: Gregory J. Pomrink, Newberry, FL (US); Zehra Tosun, Gainesville, FL (US); Cecilia A. Gao, Gainesville, FL (US); Joshua Clark, Alachua, FL (US); David C. Greenspan, Gainesville, FL (US)

(73) Assignee: NOVABONE PRODUCTS, LLC, Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/227,886

(22) Filed: Mar. 27, 2014

(65) Prior Publication Data

US 2014/0231291 A1 Aug. 21, 2014

Related U.S. Application Data

(63) Continuation of application No. 13/833,400, filed on Mar. 15, 2013, now Pat. No. 9,144,629, which is a continuation-in-part of application No. 13/039,627, filed on Mar. 3, 2011, now Pat. No. 8,795,702.

(60) Provisional application No. 61/710,332, filed on Oct. 5, 2012, provisional application No. 61/310,129, filed on Mar. 3, 2010.

(51) Int. Cl.
| | |
|---|---|
| *A61K 33/42* | (2006.01) |
| *A61K 38/39* | (2006.01) |
| *A61K 45/06* | (2006.01) |
| *A61L 27/46* | (2006.01) |
| *A61L 27/56* | (2006.01) |
| *A61L 27/24* | (2006.01) |

(52) U.S. Cl.
CPC ............... *A61L 27/46* (2013.01); *A61L 27/24* (2013.01); *A61L 27/56* (2013.01); *A61L 2430/02* (2013.01)

(58) Field of Classification Search
IPC ........ A61K 33/42,38/39, 45/06; A61L 2430/02, A61L 27/24, 27/3633, 27/365, 27/46, 27/56
See application file for complete search history.

(56) References Cited

U.S. PATENT DOCUMENTS

| | | | |
|---|---|---|---|
| 8,795,702 B2* | 8/2014 | Greenspan et al. | 424/422 |
| 2002/0112981 A1* | 8/2002 | Cooper et al. | 206/438 |
| 2004/0009598 A1* | 1/2004 | Hench et al. | 435/375 |
| 2008/0221701 A1* | 9/2008 | Zhong et al. | 623/23.62 |
| 2014/0017281 A1* | 1/2014 | Pomrink et al. | 424/400 |

* cited by examiner

*Primary Examiner* — Abigail Fisher
(74) *Attorney, Agent, or Firm* — Brinks Gilson & Lione

(57) ABSTRACT

The present invention relates to combination products including bioactive glass and collagen as well as kits comprising the same.

41 Claims, 10 Drawing Sheets

A.

B.

C.

D.

COMBINATION PRODUCTS INCLUDING BIOACTIVE GLASS AND COLLAGEN AND KITS INCLUDING THE SAME

This application is a continuation-in-part of U.S. application Ser. No. 13/833,400, filed Mar. 15, 2013, which claims priority under 35 U.S.C. §119 to U.S. Provisional Application No. 61/710,332, filed Oct. 5, 2012, and which is also a continuation-in-part of U.S. application Ser. No. 13/039,627, filed Mar. 3, 2011, which claims benefit of U.S. Provisional Application No. 61/310,129, filed Mar. 3, 2010, the entire contents of which are hereby incorporated herein by reference.

BACKGROUND OF THE INVENTION

Collagen is the main component of connective tissue and is generally found in the body as a triple helix. Collagen is also prevalent in bone. Known methods of crosslinking include introducing disulfide bonds between individual collagen molecules and fibrils. Crosslinked collagen can have enhanced mechanical attributes. The addition of crosslinked collagen to wounded tissue or bone defects may serve to provide structural support. There are various ways to crosslink collagen, such as by UV light and the use of chemical crosslinkers. Herein is provided a novel way to crosslink collagen in a manner that maintains the structure of collagen without introducing toxins that are difficult to remove.

Bioactive glass was originally developed in 1969 by L. Hench. Additionally bioactive glasses were developed as bone replacement materials, with studies showing that bioactive glass can induce or aid in osteogenesis. Hench et al, J. Biomed. Mater. Res. 5:117-141 (1971). Bioactive glass can form strong and stable bonds with bone. Piotrowski et al., J. Biomed. Mater. Res. 9:47-61 (1975). Further, bioactive glass is not considered toxic to bone or soft tissue from studies of in vitro and in vivo models. Wilson et al., J. Biomed. Mater. Res. 805-817 (1981). Exemplary bioactive glasses known in the art include 45S5, 45S5B1, 58S, and S70C30. The original bioactive glass, 45S5, is melt-derived. Sol-gel derived glasses have nanopores that allow for increased surface area and bioactivity.

U.S. Patent Application Publication No. 2002/0055143 discloses cement particles UV crosslinked with collagen.

U.S. Pat. No. 8,252,055 discloses crosslinking a collagen mineral containing composition including Bioglass.

SUMMARY OF THE INVENTION

One aspect of the invention provides for a method for crosslinking collagen. An ion-containing solution is mixed with collagen and a glass to form a paste. The paste is freeze-dried to form a composite.

Another aspect of the invention provides for a method for crosslinking collagen fibers. Water or an ion-containing solution is mixed with collagen and a glass to form a paste. The paste is freeze-dried to form a composite. The composite is immersed in water or solutions containing divalent or polyvalent metal ions. The composite is freeze-dried.

Yet another aspect of the invention provides for a method for crosslinking collagen. An ion-containing solution is mixed with collagen and a glass to form a paste. The paste is transferred to a mold. The paste is freeze-dried to form a composite.

Another aspect of the invention provides for a method for crosslinking collagen fibers. Water or an ion-containing solution is mixed with collagen and a glass to form a paste. The paste is freeze-dried to form a composite. The composite is immersed in water or solutions containing divalent or polyvalent metal ions. The composite is freeze-dried and then dried.

An aspect provides for a mixture of collagen and a glass. The mixture comprises from 60 wt. % to 90 wt. % of the glass. The collagen is crosslinked by the glass. The mixture does not comprise chitosan or an organic crosslinking agent.

The invention also provides for a crosslinked collagen material consisting of collagen and a glass. Yet another aspect of the invention provides for a crosslinked collagen material consisting of collagen, water, and a glass. Alternatively, the invention provides for a crosslinked collagen material consisting of collagen, an ion-containing solution, and a glass.

The invention also provides for a crosslinked collagen material consisting of collagen fibers and a glass. Alternatively, the invention provides for a crosslinked collagen material consisting of collagen fibers, water, and a glass. Another aspect of the invention provides for a crosslinked collagen material consisting of collagen fibers, an ion-containing solution, and a glass.

The invention provides for a combination product that includes a porous and nonporous bioactive glass and collagen. In the combination product the bioactive glass may be present in a weight ratio of from 80% to 97% in proportion to the total weight of the bioactive glass and the collagen. The combination product may include from 85 wt. % to 97.5 wt. % of the bioactive glass. The combination product may be in a form of a packable graft. The packable graft may include 75-95 wt. % bioactive glass and 5-25 wt. % collagen. The packable graft may include 85 wt. % bioactive glass and 15 wt. % collagen. In the combination product, the bioactive glass may include 55-65% 1000-2000 um bioactive glass, 10-20% 90-710 um bioactive glass, and 10-20% 32-125 um bioactive glass. In the combination product the bioactive glass may include 60% 1000-2000 um bioactive glass, 12.5% 90-710 um bioactive glass, and 12.5% 32-125 um bioactive glass. In the combination product, the 1000-2000 um bioactive glass is porous. The combination product may be in a form of a collagen bioactive glass composite. The composite may include 75-95 wt. % bioactive glass and 5-25 wt. % collagen. The composite may include 90 wt. % bioactive glass and 10 wt. % collagen. The bioactive glass of the composite may include 55-65% 1000-2000 um bioactive glass, 10-20% 90-710 um bioactive glass, and 10-20% 32-125 um bioactive glass. The bioactive glass of the composite may include 60% 1000-2000 um bioactive glass, 15% 90-710 um bioactive glass, and 15% 32-125 um bioactive glass. The 1000-2000 um bioactive glass of the composite is porous. The combination product may be in a form of a strip. The strip may include 85-97 wt. % bioactive glass and 3-15 wt. % collagen. The strip may include 95 wt. % bioactive glass and 5 wt. % collagen. The strip may include 97.5 wt. % bioactive glass and 2.5 wt. % collagen. The bioactive glass of the strip may include 53.5-73.5% 1000-2000 um bioactive glass, 10-20% 90-710 um bioactive glass, 10-20% 32-125 um bioactive glass. The bioactive glass of the strip may include 63.33% 1000-2000 um bioactive glass, 15.83% 90-710 um bioactive glass, 15.83% 32-125 um bioactive glass. The 1000-2000 um bioactive glass of the strip is porous. In the combination product, the bioactive glass may include 64.68% 1000-2000 micrometer bioactive glass, 16.16% 90-710 micrometer bioactive glass, 16.16% 32-125 micrometer bioactive glass. The combination product may further include at least one therapeutic agent, protein, or glycosaminoglycan.

Another aspect provides for a kit comprising a combination product in a form of a packable graft, composite or a strip and a packaging. The packaging may be a double peel packaging. The packaging may include an inner tray, wherein the combination product is contained within the inner tray, an inner tray lid, an outer tray, wherein the inner tray is placed in the outer tray, and an outer tray lid. The kit may further include a dispenser box. The kit may further include a syringe. The combination product may be disposed within the syringe. The syringe may include a removable cap. The syringe may be placed in the inner tray. The kit may include a syringe comprising a removable cap, wherein the syringe is sealed in a pouch.

Furthermore, the invention provides for a method for ionically crosslinking collagen. The method includes mixing an ion-containing solution with the 10 wt. % collagen and 90 wt. % bioactive glass to form a paste and freeze-drying the paste to form a composite.

BRIEF DESCRIPTIONS OF THE FIGURES

Figure 4:
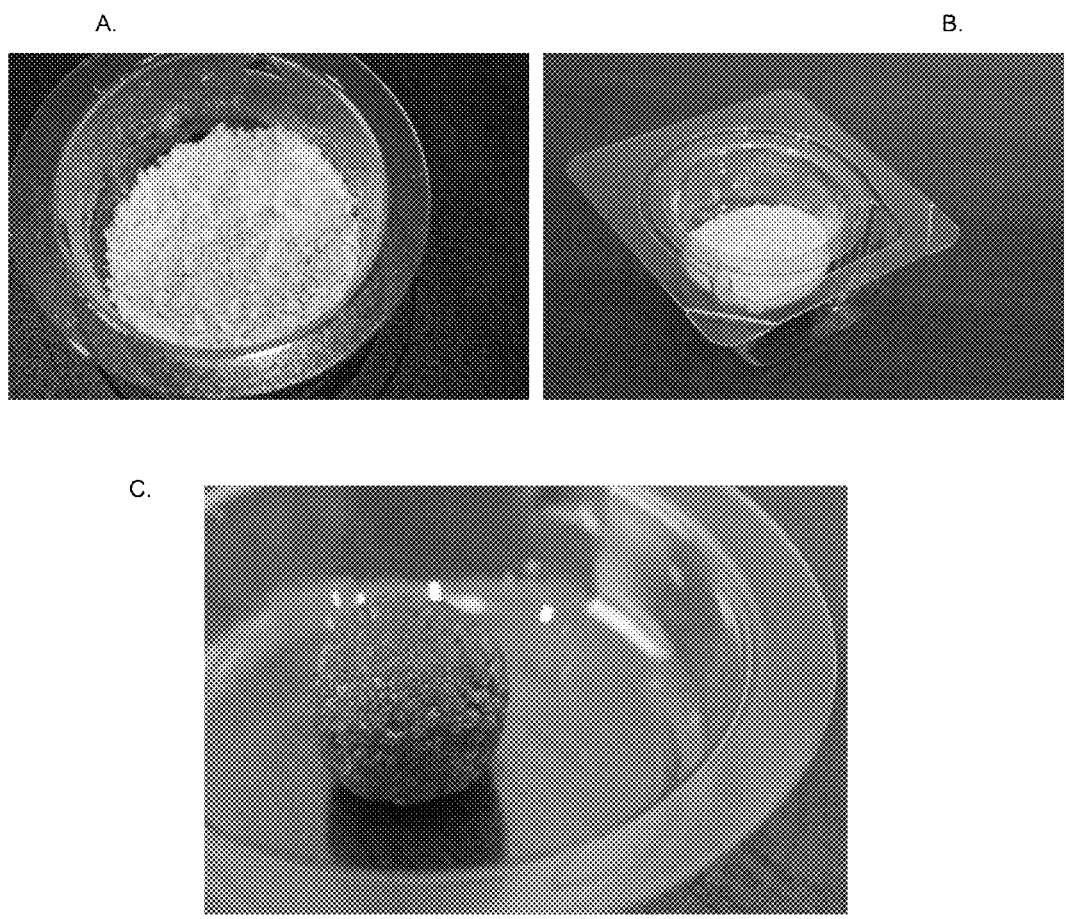

FIGS. 4 A-B are photographs depicting a CBG composite product and its packaging.

FIG. 4C is a photograph of the CBG composite product combined with a fluid.

FIG. 4 D depicts a photograph of an exemplary dispenser box.

Figure 5:
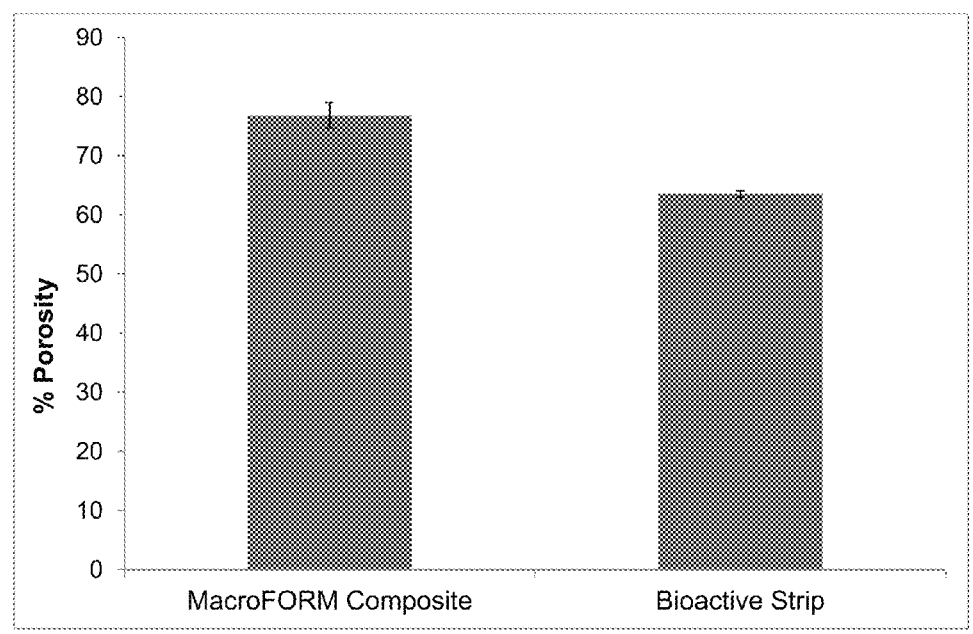

FIG. 5 depicts a bar graph showing the average porosity of MacroFORM Composite, and Bioactive Strip Lots.

Figure 6:
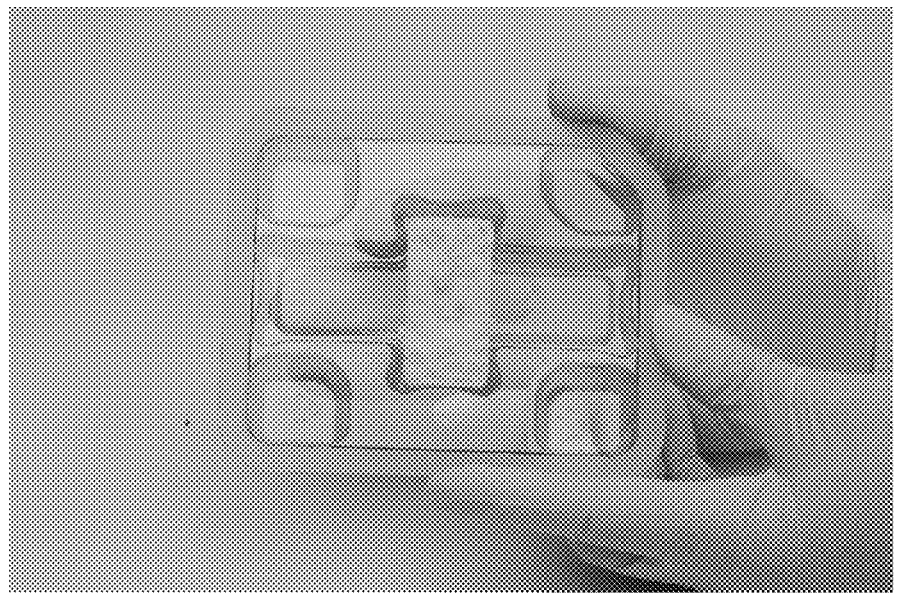
Figure 6:
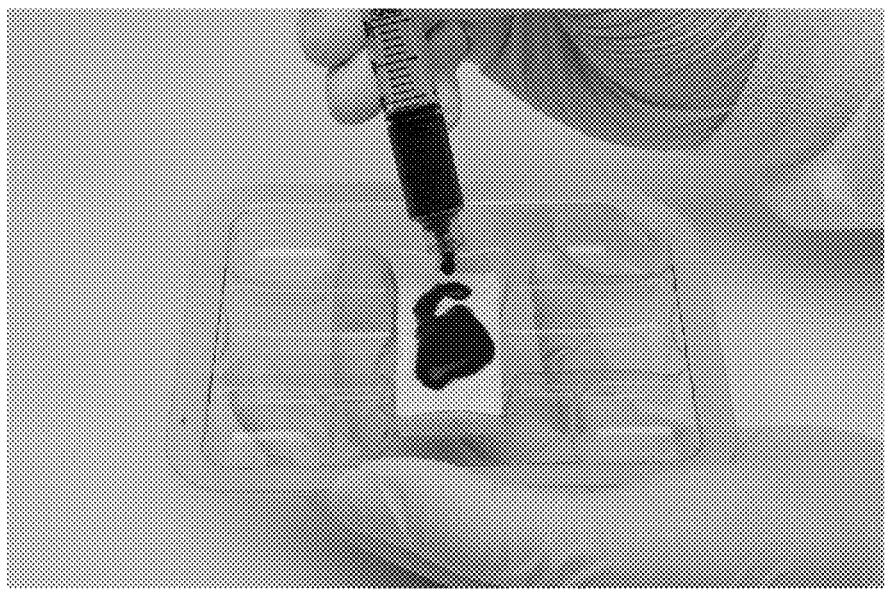
Figure 6:
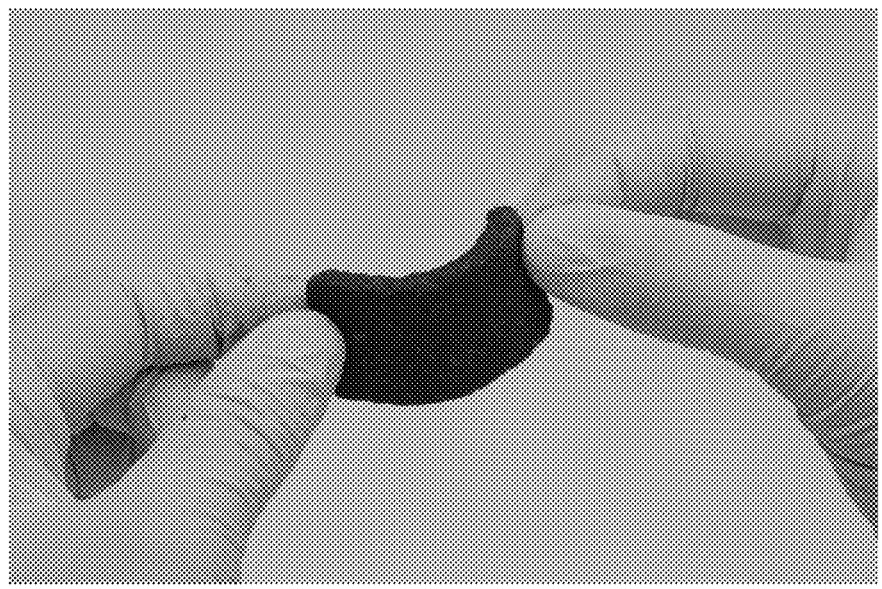
Figure 6:
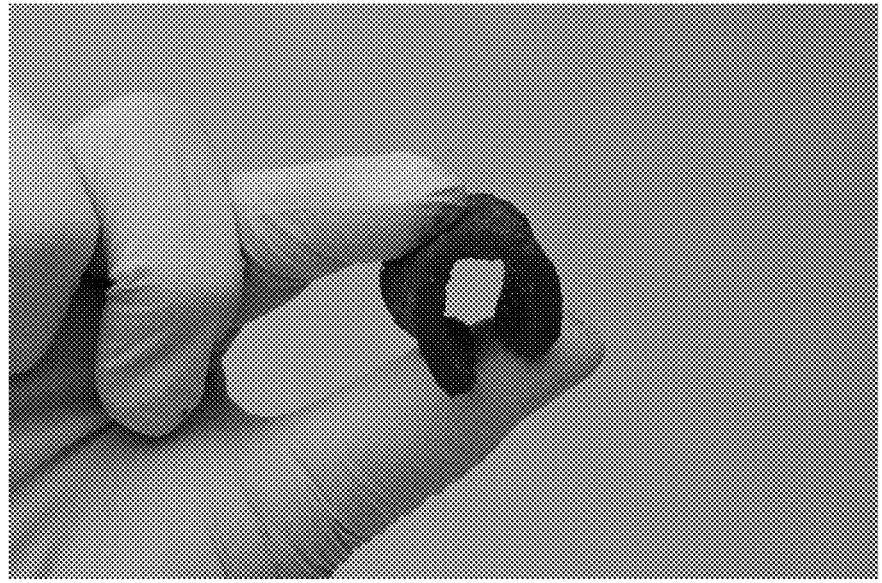

FIG. 6A is a photograph of the dry form of the exemplary CBG strip placed in its packaging.

FIG. 6B is a photograph of the exemplary CBG strip in its packaging during hydration with blood.

FIG. 6C is a photograph of the exemplary CBG strip in a hydrated state.

FIG. 6D is a photograph of the exemplary CBG strip in a hydrated state.

Figure 7:
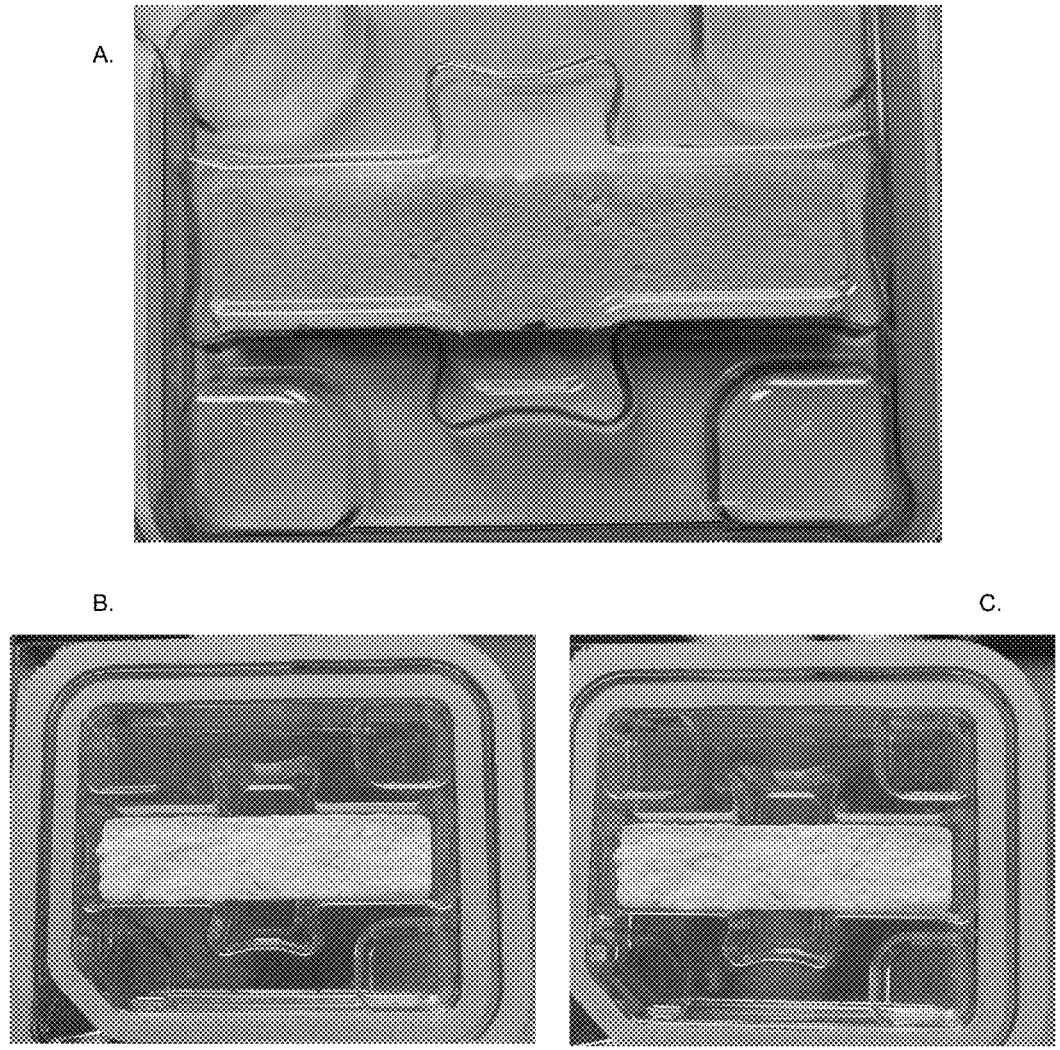

FIGS. 7A-C are photographs of the dry form of the exemplary CBG strip placed in its packaging.

Figure 8:
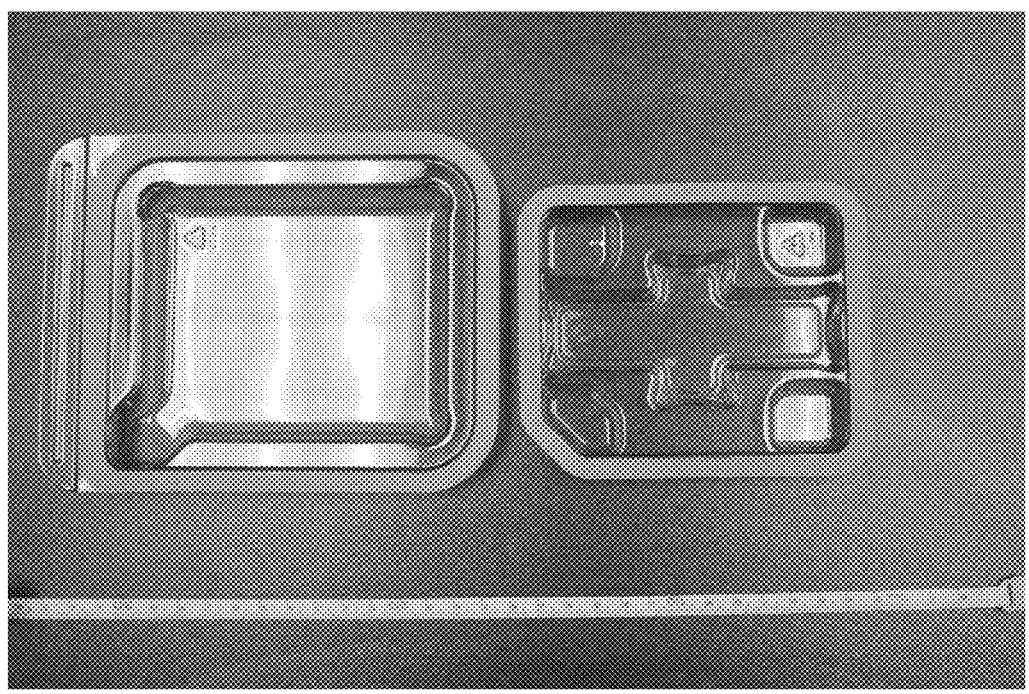

FIG. 8 is a photograph of the exemplary inner and outer trays of the packaging for the CBG strips.

DETAILED DESCRIPTION OF THE INVENTION

One aspect of the invention provides for a method for crosslinking collagen. An ion-containing solution is mixed with the collagen and bioactive glass to form a paste. The paste is freeze-dried to form a composite. In some embodiments, the method further comprises drying the composite. These steps may be performed in succession or in any order. One way in which the composite may be dried is by dehydrothermal treatment. Significant crosslinking of the collagen can occur without any drying step or dehydrothermal treatment step undertaken. Addition of the drying step or dehydrothermal treatment step can lead to enhanced crosslinking.

Bioactive glass used in the invention may be melt-derived or sol-gel derived. Depending on their composition, bioactive glasses of the invention may bind to soft tissues, hard tissues, or both soft and hard tissues. The composition of the bioactive glass may be adjusted to modulate the degree of bioactivity. Furthermore, borate may be added to bioactive glass to control the rate of degradation. Additional elements, such as barium, copper, fluorine, silver, zinc, and strontium may be added to bioactive glass to facilitate healthy bone growth or provide other desirable properties. The bioactive glass may be in the form of a particle, a glass sheet, a fiber, a mesh, or any combination of these forms.

Bioactive glass is capable of bonding to bone, which begins with the exposure of bioactive glass to aqueous solutions. Sodium ions in the glass can exchange with hydronium ions in body fluids, which increases the pH. Calcium and phosphorous ions can migrate from the glass to form a calcium and phosphate-rich surface layer. Borate ions can also migrate from the glass to from a surface layer rich in boron. Strontium ions also can migrate from the glass to form a strontium-rich surface layer. Underlying this surface layer is another layer which becomes increasingly silica rich due to the loss of sodium, calcium, strontium, boron, and/or phosphate ions (U.S. Pat. No. 4,851,046). Hydrolysis may then disrupt the Si—O—Si bridges in the silica layer to form silanol groups, which can disrupt the glass network. The glass network is then thought to form a gel in which calcium phosphate from the surface layer accumulates. Mineralization may then occur as calcium phosphate becomes crystalline hydroxyapatite, which effectively mimics the mineral layer of bones.

Bioactive glass particles, fibers, meshes or sheets may be prepared by a sol-gel method. Methods of preparing such bioactive active glasses are described in Pereira, M. et al., "Bioactive glass and hybrid scaffolds prepared by sol-gel method for bone tissue engineering" Advances in Applied Ceramics, 2005, 104(1): 35-42 and in Chen, Q. et al., "A new sol-gel process for producing $Na_2O$-containing bioactive glass ceramics" Acta Biomaterialia, 2010, 6(10):4143-4153.

The composition can be allowed to solidify. In some embodiments, particles of bioactive glass are sintered to form a porous glass.

Repeated cooling and reheating may be performed on the solidified or sintered bioactive glass, with or without spinning, to draw the bioactive glass produced into fibers. A glass drawing apparatus may be coupled to the spinner and the source of molten bioactive glass, such as molten bioactive glass present in a crucible, for the formation of bioactive glass fibers. The individual fibers can then be joined to one another, such as by use of an adhesive, to form a mesh. Alternatively, the bioactive glass in molten form may be placed in a cast or mold to form a sheet or another desired shape.

The bioactive glass particles, fibers, meshes or sheets may further comprise any one or more of adhesives, grafted bone tissue, in vitro-generated bone tissue, collagen, calcium phosphate, stabilizers, antibiotics, antibacterial agents, antimicrobials, drugs, pigments, X-ray contrast media, fillers, and other materials that facilitate grafting of bioactive glass to bone.

A bioactive glass ceramic material suitable for the present compositions and methods may have silica, sodium, calcium, strontium, phosphorous, and boron present, as well as combinations thereof. In some embodiments, sodium, boron, strontium, and calcium may each be present in the compositions in an amount of about 1% to about 99%, based on the weight of the bioactive glass ceramic. In further embodiments, sodium, boron, strontium and calcium may each be present in the composition in about 1%, about 2%, about 3%, about 4%, about 5%, about 6%, about 7%, about 8%, about 9%, or about 10%. In certain embodiments, silica, sodium, boron, and calcium may each be present in the composition in about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90 to about 95%, or about 95 to about 99%. Some embodiments may contain substantially one or two of sodium, calcium, strontium, and boron with only traces of the other(s). The term "about" as it relates to the amount of calcium phosphate present in the composition means +/−0.5%. Thus, about 5% means 5+/−0.5%. Divalent cations or ions that may be present in any of the bioactive glasses of this and other aspects of the invention include one or more of iron-II, iron-III, alumina, chromate, cobalt, tin, copper, magnesium, and zinc.

The bioactive glass materials may further comprise one or more of a silicate, borosilicate, borate, strontium, or calcium, including SrO, CaO, $P_2O_5$, $SiO_2$, and $B_2O_3$. An exemplary bioactive glass is 45S5, which includes 46.1 mol % $SiO_2$, 26.9 mol % CaO, 24.4 mol % $Na_2O$ and 2.5 mol % $P_2O_5$. An exemplary borate bioactive glass is 45S5B1, in which the $SiO_2$ of 45S5 bioactive glass is replaced by $B_2O_3$. Other exemplary bioactive glasses include 58S, which includes 60 mol % $SiO_2$, 36 mol % CaO and 4 mol % $P_2O_5$, and S70C30, which includes 70 mol % $SiO_2$ and 30 mol % CaO. In any of these or other bioactive glass materials of the invention, SrO may be substituted for CaO.

The following composition, having a weight % of each element in oxide form in the range indicated, will provide one of several bioactive glass compositions that may be used to form a bioactive glass ceramic:

| | |
|---|---|
| $SiO_2$ | 0-86 |
| CaO | 4-35 |
| $Na_2O$ | 0-35 |
| $P_2O_5$ | 2-15 |
| $CaF_2$ | 0-25 |
| $B_2O_3$ | 0-75 |
| $K_2O$ | 0-8 |
| MgO | 0-5 |
| CaF | 0-35 |

In some embodiments, the particles are sintered to form porous particulate made from the bioactive glass particles. In one embodiment, fine particles of the bioactive glass are mixed with a sacrificial polymer and a binder to create a pre-shaped construct (e.g., a block or disk). The construct is then heated under specific conditions that allow a welding of the particles together without completely melting them. This process uses a temperature high enough to allow for the polymer material to burn off leaving a porous structure. The compression strength as well as the porosity of the construct may be controlled by varying the type and the amount of the sacrificial polymer and the sintering time and temperature used. Porosities as high as 90% may be achieved under suitable conditions. The pores in the bioactive glass material range from about 10 microns to about 5100 microns with an average pore size of 100±50 microns, 200±50 microns, 300±50 microns, 400±50 microns, 500±50 microns, 600±50 microns or 700±50 microns.

The bioactive glass ceramic can be in the form of a three-dimensional compressible body of loose glass-based fibers in which the fibers comprise one or more glass-formers selected from the group consisting of $P_2O_5$, $SiO_2$, and $B_2O_3$. Some of the fibers have a diameter between about 100 nm and about 10,000 nm, and a length:width aspect ratio of at least about 10. The pH of the bioactive glass can be adjusted as-needed.

In some embodiments, the body comprises fibers having a diameter between about 100 nm and about 10,000 nm. The especially small diameter of these fibers renders them highly flexible so they form into the compressible body without breaking. In some embodiments the body includes fibers meeting these dimensional requirements in addition to other glass morphologies, such as fibers of other dimensions, spheres, microspheres, particles, ribbons, flakes or the like. The fibers may have a variety of cross section shapes, such as flat, circular, oval, or non-circular.

In any of the various aspects and embodiments of the invention, the bioactive glass/collagen mixture may be in the form of a "CBG packable graft", which as defined herein is a loose collagen and 45S5 bioactive glass mixture that becomes moldable when hydrated. Alternatively, in any of the various aspects and embodiments of the invention, the bioactive glass/collagen mixture may be in the form of a "CBG composite," which as defined herein is collagen and 45S5 bioactive glass that is lyophilized once into a specific shape. Alternatively, in any of the various aspects and embodiments of the invention, the bioactive glass/collagen mixture may be in the form of a "CBG strip," which as defined herein is collagen and 45S5 bioactive glass that is lyophilized into a rectangular shape and undergoes additional processing.

The three CBG combination products, CBG packable graft, CBG composite and CBG strip are designed to facilitate the repair of skeletal defects. The CBG products have a three-dimensional network of pores that resembles the structure of human cancellous bone. The three-dimensional pore structure of the CBG products quickly imbibes and retains fluids, making it easy to combine with saline, blood and/or bone marrow aspirate.

The CBG products guide the regeneration of bone across a critical defect site into which the product is implanted. New bone forms within the implant when the graft is placed in direct contact with viable host bone. Ultimately, the CBG product is resorbed and remodeled into bone.

In certain embodiments, the CBG products are intended to be used alone or combined with saline, autograft, allograft, blood, or bone marrow aspirate, and are intended for use as a bone void filler to fill voids or gaps of the skeletal system not intrinsic to the stability of the bony structure. Furthermore, the packaging of the CBG products is designed to facilitate such mixing with saline, autograft, allograft, blood, or bone marrow aspirate The CBG product retains shape after hydration with saline, blood or bone marrow. Also, the CBG products are flexible, as shown in FIGS. 6C-D.

In certain other embodiments, the CBG product is also intended for use in the treatment of surgically treated osseous defects or osseous defects created from traumatic injury to the bone.

In certain embodiments, the CBG products possess inter-particle spaces to facilitate the integration of liquid (i.e., blood, bone marrow aspirate, etc.) into the structure in less than, e.g., about 3 min.

Following placement in the bony void or gap (defect), the CBG product is resorbed and replaced with bone during the healing process.

In preferred embodiments, the CBG product is provided sterile, non-pyrogenic, and prepared in a double peel package (as shown, e.g., in FIGS. 7A-C and FIG. 8) and is intended for a single use by, e.g., surgeons, and preferably, orthopedic surgeons.

MacroFORM Packable Graft

Certain embodiments relate to a packable graft, which is a bioresorbable bone graft material that includes a porous and crystalline bioactive glass, such as 45S5 Bioactive Glass (Bioglass®) in combination with collagen. In preferred embodiments, the packable graft are provided sterile, non-pyrogenic, and prepared in double peel packages as intended for single use (FIG. 4).

In certain preferred embodiments, the packable graft includes a bioactive glass that includes approximately 75-95% by weight bioactive glass; approximately 85-95% by weight bioactive glass; approximately 85-90% by weight bioactive glass; or approximately 85-87% by weight bioactive glass. In certain embodiments, the packable graft includes a bioactive glass that includes at least approximately 75%, 76%, 77%, 78%, 79%, 80%, 81%, 82%, 83%, 84%, 85%, 86%, 87%, 88%, 89%, 90%, 91%, 92%, 93%, 94%, or 95% by weight bioactive glass. In a preferred embodiment, the packable graft includes bioactive glass that includes approximately 85% by weight bioactive glass, such as 45S5 Bioactive Glass (Bioglass®).

The bioactive glass can include approximately 55-65% 1000-2000 um porous glass, approximately 55-62% 1000-2000 um porous glass, approximately 55-60% 1000-2000 um porous glass, or approximately 57-60% 1000-2000 um porous glass; approximately 10-20% 90-710 um nonporous glass, approximately 10-15% 90-710 um nonporous glass, approximately 12-14% 90-710 um nonporous glass, or approximately 12-13% 90-710 um nonporous glass; and approximately 10-20% 32-125 um nonporous glass, approximately 10-15% 32-125 um nonporous glass, approximately 12-14% 32-125 um nonporous glass, or approximately 12-13% 32-125 um nonporous glass. In one preferred embodiment, the bioactive glass includes approximately 60% 1000-2000 um porous glass, approximately 12.5% 90-710 um nonporous glass, and approximately 12.5% 32-125 um nonporous glass.

In certain embodiments, the bioactive glass is not cross-linked.

In certain embodiments, the bioactive glass may consist of amorphous, crystalline, or a mixture of both types of particles or a material possessing both, amorphous and crystalline domains of various sizes ranging from 32-2000 um.

In certain embodiments, the particles may be porous particles.

In certain preferred embodiments, the composition of the bioactive glass may include $SiO_2$—about 45.0±2.0 wt %; $Na_2O$—about 24.5±2.0 wt %; CaO—about 24.5±2.0 wt %; and about $P_2O_5$—6.0±1.0 wt %.

The Packable grafts also include approximately 5-25% by weight collagen; preferably, about 5-20% by weight collagen, more preferably about 10-20% by weight collagen, most preferably about 15% by weight collagen. Collagen may be synthetic or sourced from mammalian or non-mammalian species including rats, humans and fish. Preferably, high purity type I collagen from bovine hide (manufactured by Devro Pty Ltd., Bathurst, New South Wales, Australia; distributed in the United States by Collagen Solutions, LLC. San Jose, Calif.) is used according to the preferred embodiments of the present invention. The collagen complies with FDA guidance for Medical Devices Containing Materials Derived from Animal Sources as well as with EU Directive 2003/32/EC.

MACROFORM Composite

Certain embodiments relate to a MACROFORM composite, which is a bioresorbable bone graft material that includes a porous and crystalline bioactive glass, such as 45S5 Bioactive Glass (Bioglass®) in combination with collagen.

In certain preferred embodiments, the MACROFORM composite include a bioactive glass that includes approximately 75-95% by weight bioactive glass, approximately 80-95% by weight bioactive glass; approximately 85-95% by weight bioactive glass; or approximately 85-90% by weight bioactive glass. In certain embodiments, the packable graft includes a bioactive glass that includes at least approximately 75%, 76%, 77%, 78%, 79%, 80%, 81%, 82%, 83%, 84%, 85%, 86%, 87%, 88%, 89%, 90%, 91%, 92%, 93%, 94%, or 95% by weight bioactive glass. In a preferred embodiment, the MACROFORM composite include a bioactive glass that includes approximately 90% by weight bioactive glass, such as 45S5 Bioactive Glass (Bioglass®).

The bioactive glass can include approximately 55-65% 1000-2000 um porous glass, approximately 57-65% 1000-2000 um porous glass, approximately 55-60% 1000-2000 um porous glass, or approximately 60-65% 1000-2000 um porous glass; approximately 10-20% 90-710 um nonporous glass, approximately 10-15% 90-710 um nonporous glass, approximately 12-14% 90-710 um nonporous glass, or approximately 12-13% 90-710 um nonporous glass; and approximately 10-20% 32-125 um nonporous glass, approximately 10-15% 32-125 um nonporous glass, approximately 12-14% 32-125 um nonporous glass, or approximately 12-13% 32-125 um nonporous glass. In a preferred embodiment, the bioactive glass includes approximately 60% 1000-2000 um porous glass, approximately 15% 90-710 um nonporous glass, and approximately 15% 32-125 um nonporous glass.

In certain embodiments, the bioactive glass is not crosslinked.

In certain embodiments, the bioactive glass may consist of amorphous, crystalline, or a mixture of both types of particles or a material possessing both, amorphous and crystalline domains of various sizes ranging from 32-2000 um.

In certain embodiments, the particles may be porous particles.

In certain preferred embodiments, the composition of the bioactive glass may include $SiO_2$—about 45.0±2.0 wt %; $Na_2O$—about 24.5±2.0 wt %; CaO—about 24.5±2.0 wt %; and about $P_2O_5$—6.0±1.0 wt %.

The composite also includes approximately 5-25% by weight collagen; preferably, about 5-20% by weight collagen, more preferably about 10-20% by weight collagen, most preferably, approximately 10% by weight collagen. Collagen may be synthetic or sourced from mammalian or non-mammalian species including rats, humans and fish. Preferably, high purity type I collagen from bovine hide (manufactured by Devro Pty Ltd., Bathurst, New South Wales, Australia; distributed in the United States by Collagen Solutions, LLC. San Jose, Calif.) is used according to the preferred embodiments of the present invention. The collagen complies with FDA guidance for Medical Devices Containing Materials Derived from Animal Sources as well as with EU Directive 2003/32/EC.

CBG Strip

Certain other embodiments relate to a CBG strip, which includes approximately 85-97% by weight bioactive glass; approximately 85-95% by weight bioactive glass; approximately 85-90% by weight bioactive glass; or approximately 85-87% by weight bioactive glass. In certain embodiments, the packable graft includes a bioactive glass that includes at least approximately 85%, 86%, 87%, 88%, 89%, 90%, 91%, 92%, 93%, 94%, 95%, 96%, or 97% by weight bioactive glass, such as 45S5 bioactive glass (Bioglass®). In a preferred embodiment, the CBG strip includes 95% by weight bioactive glass, such as 45S5 Bioactive Glass (Bioglass®) and collagen.

The bioactive glass includes approximately 53.5-73.5% 1000-2000 um porous glass, approximately 60-70% 1000-2000 um porous glass, approximately 60-65% 1000-2000 um porous glass, or approximately 63-64% 1000-2000 um porous glass; approximately 10-20% 90-710 um nonporous glass, approximately 15-20% 90-710 um nonporous glass, approximately 15-18% 90-710 um nonporous glass, or approximately 15-16% 90-710 um nonporous glass; and approximately 10-20% 32-125 um nonporous glass, approximately 15-20% 32-125 um nonporous glass, approximately 15-18% 32-125 um nonporous glass, or approximately 15-16% 32-125 um nonporous glass. In certain preferred embodiments, the bioactive glass includes approximately 63.33% 1000-2000 um porous glass, approximately 15.83% 90-710 um nonporous glass, and approximately 15.83% 32-125 um nonporous glass.

In certain embodiments, the bioactive glass is not crosslinked.

In certain embodiments, the bioactive glass may consist of amorphous, crystalline, or a mixture of both types of particles or a material possessing both, amorphous and crystalline domains of various sizes ranging from 32-2000 um.

In certain embodiments, the particles may be porous particles.

The composition of the bioactive glass includes $SiO_2$— approximately 45.0±2.0 wt %; $Na_2O$—approximately 24.5±2.0 wt %, CaO—approximately 24.5±2.0 wt %, and $P_2O_5$—approximately 6.0±1.0 wt %.

The strip also includes approximately 3-15% by weight collagen; preferably, approximately 5% by weight collagen. Collagen may be synthetic or sourced from mammalian or non-mammalian species including rats, humans and fish. Preferably, high purity type I collagen from bovine tendon (manufactured by Southern Lights Biomaterials 163 Tennyson Street, Napier 4110, New Zealand) is used according to the preferred embodiments of the present invention. The collagen complies with FDA guidance for Medical Devices Containing Materials Derived from Animal Sources as well as with EU Directive 2003/32/EC.

Examples of CBG strips are shown in FIGS. 6A-D. As shown specifically, in FIGS. 6C-D, the CBG strip is very flexible and able to retain shape once hydrated with blood or other fluid.

In any of the various aspects and embodiments of the invention, various therapeutic agents, including growth factors, antibiotics or the like, and other bioactive materials including proteins and glycosaminoglycans may be added during the manufacturing process of the bioactive glass/collagen mixture and/or products. Alternatively, various therapeutic agents and other bioactive materials including proteins and glycosaminoglycans may be added immediately prior to or concurrently with the implantation of the bioactive glass/collagen mixture and/or products.

Kits

The CBG packable graft, composite and strips may be packaged for terminally sterilized medical devices.

In certain embodiments, the MACROFORM packable graft, composite and strips may be packaged into a kit. The packaging is easy to open and use in sterile surgical environment. The packaging and product labeling is easy to read. The kit may further include a product insert including directions for use.

In certain preferred embodiments, as shown in FIGS. 7A-C and FIG. 8, the packaging for the CBG packable graft, composite and strips includes an inner tray to hold CBG packable graft, composite or strip. The packaging may further include an inner tray lid, such as a foil laminate or Tyvek® to seal the product in the inner tray (see e.g., FIG. 7A). The packaging material and seal areas may be identical. Alternatively, the packaging material and seal areas may be different. Exemplary packaging materials include Polyethylene terephthalate glycol-modified (PETG) tray materials (manufactured by, e.g., Eastman Chemical, SK Chemicals and Artenius Italia). Although, PETG is the most common and preferred material for use as the packaging material, other tray materials may also be used. For example, the lids may be made from foil laminates or Tyvek, depending on the mode of sterilization to be employed for the CBG products of the present invention.

The packaging may also include an outer tray that contains the inner tray and an outer tray lid (FIGS. 7B-C and FIG. 8). The packaging materials and seal areas may be identical or different.

In certain embodiments, both, the inner and outer tray of the packaging is labeled.

The CBG products may be available in various shapes and sizes.

Some exemplary shapes for the CBG composite product include: 15 mm height×10 mm diameter; 15 mm height×15 mm diameter; 50 mm length×25 mm width×4 mm height; 50 mm length×25 mm width×8 mm height; 100 mm length×25 mm width×4 mm height; 100 mm length×25 mm width×6 mm height; and 100 mm length×25 mm width×8 mm height.

The CBG composite product's weight may vary depending upon size as follows: 0.4-1.1 grams for 15 mm height×10 mm diameter; 1.2-1.9 grams for 15 mm height×15 mm diameter; 2.0-3.9 grams for 50 mm length×25 mm width×4 mm height; 4.0-6.9 grams for 50 mm length×25 mm width×8 mm height; 4.0-6.9 grams for 100 mm length×25 mm width×4 mm height; 7.0-9.9 grams for 100 mm length×25 mm width×6 mm height; and 10.0-14.0 grams for 100 mm length×25 mm width×8 mm height.

The strips may be of varying shapes and sizes. For example, the strips may be: 1.0 cc (10 mm height×15 mm diameter), 2.5 cc (15 mm height×15 mm diameter), 5.0 cc (50 mm length×25 mm width×4 mm height), 10.0 cc (50 mm length×25 mm width×8 mm height), 10.0 cc (100 mm length×25 mm width×4 mm height), 15.0 cc (100 mm length×25 mm width×6 mm height), and 20.0 cc (100 mm length×25 mm width×8 mm height).

The product weight for the CBG strips will vary depending upon size as follows: 1.0 cc: 0.6-1.5 grams, 2.5 cc: 2.0-2.9 grams, 5.0 cc: 4.1-6.5 grams, 10.0S cc: 7.8-11.1 grams, 10.0 L cc: 7.8-11.1 grams, 15.0 cc: 12.5-15.3 grams, and 20.0 cc: 13.8-16.7 grams.

Figure 4D:
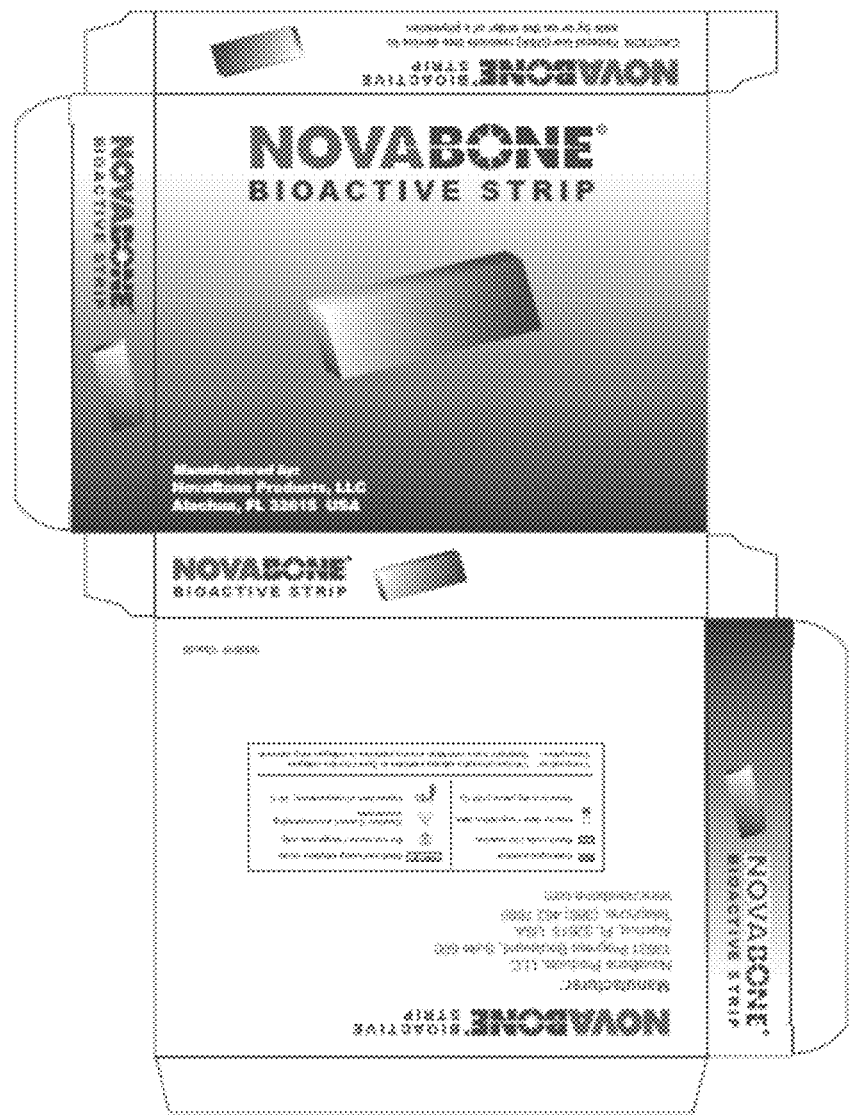

In certain embodiments, the packaging also includes a dispenser box, as shown in FIG. 4D. The dispenser box may be of various shapes and sizes, including 1.0 cc, 2.5 cc, 5.0 cc, 10.0 cc (short), 10.0 cc (long), 15.0 cc, and 20.0 cc.

In certain embodiments, the kits may further include a biopsy needle, such as Jamshidi needle, which is a cylindrical, trephine needle with a tapered cutting tip. Exemplary biopsy needles were previously described in U.S. Pat. No. 4,356,828, which is incorporated by reference herein in its entirety.

In certain embodiments, the CBG material may be packaged in a syringe, syringe which attaches to a biopsy needle to facilitate hydration with blood or bone marrow. The syringe may have a removable cap to allow delivery of the hydrated material.

In certain embodiments, the combination products described herein may be disposed within a syringe, The syringe may be placed directly in a tray (e.g., inner tray) for packaging into a kit. Alternatively, the syringe may be first sealed in a pouch and then packaged into a kit.

Bioactive glass ceramics may be prepared by heating a composition comprising one or more of $SiO_2$, $CaH(PO_4)$, CaO, $P_2O$, $Na_2O$, $CaCO_3$, $Na_2CO_3$, $K_2CO_3$, MgO, and $H_2BO_3$ to a temperature between 1300 and 1500° C. such that the composition may form molten glass. An exemplary composition that can form fibers includes 40-60% $SiO_2$, 10-20%

CaO, 0-4% $P_2O_5$, and 19-30% NaO. Other exemplary compositions include 45S5, which includes 46.1 mol % $SiO_2$, 26.9 mol % Ca), 24.4 mol % $Na_2O$ and 2.5 mol % $P_2O_5$; 45S5B1, which includes 46.1 mol % $B_2O_3$, 26.9 mol % Ca), 24.4 mol % $Na_2O$ and 2.5 mol % $P_2O_5$; 58S, which includes 60 mol % $SiO_2$, 36 mol % CaO and 4 mol % $P_2O_5$; and S70C30, which includes 70 mol % $SiO_2$ and 30 mol % CaO. Another exemplary composition includes 40 mol % $SiO_2$, 40 mol % $B_2O_3$, 20 mol % CaO, and 20 mol % $Na_2O$.

In this and other aspects of the invention, dehydrothermal treatment may involve the removal of water from collagen. Various methods of dehydrothermal treatment of collagen are known in the art. Dehydrothermal treatment generally involves application of moderate heat under vacuum to remove water from the collagen. Crosslinking can result from dehydrothermal treatment by a dehydration reaction in which a hydroxyl group from one collagen molecule is combined with a proton from another collagen molecule. It is noted that in the various aspects and embodiments of the invention, significant crosslinking of the collagen can occur without dehydrothermal treatment.

In some embodiments, the steps are carried out in succession as follows. Water or an ion-containing solution is first mixed with the collagen and bioactive glass to form a paste. The paste is then freeze-dried to form a composite. Then, the composite is dried, such as by dehydrothermal treatment. It is noted that significant crosslinking of the collagen can occur without any drying step or dehydrothermal treatment step undertaken.

Optional soaking steps may be undertaken before and/or after one or more of each of the lyophilization, freeze-drying or dehydrothermal treatments. The bioactive glass, collagen, pastes, and/or composites may be soaked in solutions that include reverse osmosis deionized water, PBS, $Fe_2(SO_4)_3$, or any other suitable buffer.

The collagen is in the form of fibers suspended in aqueous solution. In some embodiments, the bioactive glass is present in a weight ratio of from 80% to 90% in proportion to the total weight of the bioactive glass and the collagen. The weight ratio of bioactive glass may be about 80%, about 81%, about 82%, about 83%, about 84%, about 85%, about 86%, about 87%, about 88%, about 89%, or about 90% in proportion to the total weight of the bioactive glass and the collagen.

In some embodiments of this and other aspects of the invention, the composite is ionically-crosslinked. Incubation of collagen in a solution containing divalent cations is effective to crosslink collagen. The divalent cations can be one or more of $Ca^{2+}$, $Mg^{2+}$, $Fe^{2+}$, $Sr^{2+}$, $Cd^{2+}$, $Co^{2+}$, $Mn^{2+}$, $Ni^{2+}$, and $Zn^{2+}$. The divalent cations may be leached from glass that is submerged in water or an aqueous ion-containing solution. For example, a bioactive glass submerged in water can leach calcium and/or strontium ions.

In certain other embodiments, polyvalent (3+ or higher) metal ions may also be released from the glass that is submerged in water or an aqueous ion-containing solution. The polyvalent metal ions may include $Al^{3+}$, $Fe^{3+}$, $V^{4+}$, $Ti^{4+}$ and $Zr^{4+}$.

In some embodiments of this and other aspects of the invention, the mechanical properties of the composite, or material, are tested. For instance, the tensile strength may be measured, for example, if the composite is in the form of fibers. Methods of measuring tensile strength are known in the art, such as described in ASTM-D 638, which is incorporated by reference herein in its entirety. The compressive strength, or ability of the composite or material to resist compression, may also be measured. Methods of measuring compressive strength are known in the art, such as described in ASTM-D 695, which is incorporated by reference herein in its entirety. Also, the flexural strength of the material may be tested, such as described in Goudouri, et al., "Dental Ceramics/Bioactive Glass Composites: Characterization and Mechanical Properties Investigation" Bioceramics Dev. App. 2011, (1):1-4, incorporated by reference in its entirety herein.

Another aspect of the invention provides for a method for crosslinking collagen. Water or an ion-containing solution is mixed with collagen and a glass to form a paste. The paste is freeze-dried to form a composite. The method may further comprise drying the composite, such as by dehydrothermal treatment. The dehydrothermal treatment step is not required, however, for significant crosslinking to occur. These steps may be performed in succession or in any order. The glass may be such that it is capable of releasing divalent cations in the presence of water. Some exemplary glasses include a blend of ionomer glass with a 45S5 bioactive glass and a slurry of a 1% $CaCl_2$ solution at pH 6.5 with a 45S5 bioactive glass. If the glass releases divalent or polyvalent cations, these may be one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$.

In some embodiments, the steps are carried out in succession as follows. Water or an ion-containing solution is first mixed with collagen and a glass to form a paste. The paste is then freeze-dried to form a composite. After freeze-drying, the composite may optionally be dried, such as by dehydrothermal treatment. The dehydrothermal treatment step is not required, however, for significant crosslinking to occur.

Optional soaking steps may be undertaken before and/or after one or more of each of the lyophilization, freeze-drying, or dehydrothermal treatments. The bioactive glass, collagen, pastes, and/or composites may be soaked in solutions that include reverse osmosis deionized water, PBS, $Fe_2(SO_4)_3$, or any other suitable buffer.

In some embodiments, collagen is in the form of collagen fibers suspended in aqueous solution.

The composite formed in any of the embodiments of this aspect may be ionically-crosslinked. The ionic crosslinking can occur by means of the various methods and embodiments described herein, such as by incubating the composite in bioactive glass. In some embodiments, the composite comprises from 60 wt. % to 95 wt. % of the glass, from 65 wt. % to 90 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

Another aspect of the invention provides for a method for crosslinking collagen fibers. Water or an ion-containing solution is mixed with collagen and a glass to form a paste. The paste is freeze-dried to form a composite. The composite is immersed in water or solutions containing divalent or polyvalent metal ions. The immersion may be from 3 to 24 hours. The composite is freeze-dried. In some embodiments, collagen is in the form of fibers suspended in aqueous solution. These steps may be performed in succession or in any order.

The method may further comprise drying the composite, such as by dehydrothermal treatment. The dehydrothermal treatment step is not required, however, for significant crosslinking to occur. In some embodiments, the glass is capable of releasing divalent cations in the presence of water. Some exemplary divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass. The composite may be ionically-crosslinked.

Optional soaking steps may be undertaken before and/or after one or more of each of the lyophilization, freeze-drying or dehydrothermal treatments. The bioactive glass, collagen, pastes, and/or composites may be soaked in solutions that include reverse osmosis deionized water, PBS, $Fe_2(SO_4)_3$, or any other suitable buffer.

In some embodiments, the composite comprises from 60 wt. % to 95 wt. % of the glass, from 65 wt. % to 90 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

Another aspect of the invention provides for a method for crosslinking collagen fibers. Water or an ion-containing solution is mixed with collagen and a glass to form a paste. The paste is freeze-dried to form a composite. The composite is immersed in water or solutions containing divalent or polyvalent metal ions. The composite is freeze-dried and then dried. These steps may be performed in succession or in any order.

In some embodiments of this aspect, the method further comprises drying the composite. The drying may be conducted by dehydrothermal treatment. The dehydrothermal treatment step is not required, however, for significant crosslinking to occur. In some embodiments, the glass is capable of releasing divalent cations in the presence of water. Some exemplary divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$.

In some embodiments, the glass is a bioactive glass, such as those described in the above aspect of the invention.

In some embodiments, the mechanical properties of the composite are tested. The ways in which mechanical properties are tested include those discussed in other aspects of the invention.

In some embodiments, collagen is in the form of collagen fibers suspended in aqueous solution.

In some embodiments, the immersion of the composite in water or solutions containing divalent or polyvalent metal ions is conducted from 3 to 24 hours. The immersion may be conducted for about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments of this aspect, the composite is ionically-crosslinked by any of the various methods described herein, such as by incubating the composite in a solution having divalent cations. An exemplary solution is calcium chloride. The calcium chloride may be in a concentration ranging from 0.1% to 1%, such as 0.1%, 0.2%, 0.25%, 0.3%, 0.4%, 0.5%, 0.6%, 0.7%, 0.8%, 0.9%, and 1.0%. The calcium chloride solution may be at any pH, such as pH 6.5 or pH 7.0. Crosslinking may also be enhanced by adding ionomer glasses, such as TF-325 in powder form.

Optional soaking steps may be undertaken before and/or after one or more of each of the lyophilization or dehydrothermal treatments. The bioactive glass, collagen, pastes, and/or composites may be soaked in solutions that include reverse osmosis deionized water, PBS, $Fe_2(SO_4)_3$, or any other suitable buffer.

In some embodiments of this aspect, the composite comprises from 60 wt. % to 90 wt. % of the glass, from 65 wt. % to 95 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

Yet another aspect of the invention provides for a method for crosslinking collagen. An ion-containing solution is mixed with collagen and a glass to form a paste. The paste is transferred to a mold. The paste is freeze-dried to form a composite.

In some embodiments of this aspect, the method further comprises drying the composite. The drying may be conducted by dehydrothermal treatment. The dehydrothermal treatment step is not required, however, for significant crosslinking to occur. In some embodiments, the glass is capable of releasing divalent cations in the presence of water. Some exemplary divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$.

In some embodiments, the glass is a bioactive glass. The bioactive glass may be one or more of the various bioactive glasses described herein. In some embodiments, the bioactive glass may be 45S5. Crosslinking may also be enhanced by adding ionomer glass, such as TF-325 in powder form.

Optional soaking steps may be undertaken before and/or after one or more of each of the lyophilization, freeze-drying or dehydrothermal treatments. The bioactive glass, collagen, pastes, and/or composites may be soaked in solutions that include reverse osmosis deionized water, PBS, $Fe_2(SO_4)_3$, or any other suitable buffer.

In some embodiments, the mechanical properties of the composite are tested. The ways in which mechanical properties are tested include those discussed in other aspects of the invention.

The collagen may be in the form of collagen particles or fibers suspended in aqueous solution or a dispersion of acid swollen collagen fibers.

In some embodiments, the immersion of the composite in water or solutions containing divalent or polyvalent metal ions is conducted from 3 to 24 hours. The immersion may be conducted for about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments of this aspect, the composite is ionically-crosslinked. The crosslinking may arise from the presence of divalent cations, as discussed above.

In some embodiments of this aspect, the composite comprises from 60 wt. % to 95 wt. % of the glass, from 65 wt. % to 90 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

The invention also provides for a mixture of collagen and a glass. The mixture comprises from 60 wt. % to 90 wt. % of the glass. The collagen is crosslinked by the glass. The mixture does not comprise chitosan or an organic crosslinking agent. In some embodiments of this aspect, the mixture further comprises water. The glass may be capable of releasing divalent cations in the presence of water. In some embodiments, the divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. In some embodiments, the glass is a bioactive glass.

In some embodiments of this aspect, the composite comprises from 60 wt. % to 90 wt. % of the glass, from 65 wt. % to 95 wt. % of the glass, from 70 wt. % to 90 wt. % of the glass, from 75 wt. % to 90 wt. % of the glass, or from 80 wt. % to 90 wt. % of the glass. In some embodiments, the weight ratio of the bioactive glass in the composite may be about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

In some embodiments, the glass is capable of releasing divalent cations in the presence of water. The divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well. Crosslinking may also be enhanced by adding ionomer glasses, such as TF-325 in powder form.

Another aspect of the invention provides for a crosslinked collagen material consisting of collagen and a glass. The material comprises from 60 wt. % to 97.5 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 97.5% of the glass by weight.

In some embodiments, the glass is capable of releasing divalent cations in the presence of water. The divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well.

Yet another aspect of the invention provides for a crosslinked collagen material consisting of collagen, water, and a glass. The material may comprise from 60 wt. % to 97.5 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 97.5% of the glass by weight.

In some embodiments, the glass is capable of releasing divalent cations in the presence of water. The divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well. Crosslinking may also be enhanced by adding ionomer glass, such as TF-325 in powder form.

Optional soaking steps may be undertaken before and/or after one or more of each of the lyophilization, freeze-drying or dehydrothermal treatments. The bioactive glass, collagen, pastes, and/or composites may be soaked in solutions that include reverse osmosis deionized water, PBS, $Fe_2(SO_4)_3$, or any other suitable buffer.

Yet another aspect of the invention provides for a crosslinked collagen material consisting of collagen, water, ions, and a glass. The material comprises from 60 wt. % to 97.5 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 97.5% of the glass by weight.

In some embodiments, the glass is capable of releasing divalent cations in the presence of water. The divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well.

Another aspect of the invention provides for a crosslinked collagen material consisting of collagen fibers and a glass. The material comprises from 60 wt. % to 97.5 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 97.5% of the glass by weight.

In some embodiments, the glass is capable of releasing divalent cations in the presence of water. The divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass as well.

Yet another aspect of the invention provides for a crosslinked collagen material consisting of collagen fibers, water, and a glass. The material comprises from 60 wt. % to 97.5 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 97.5% of the glass by weight.

In some embodiments, the glass is capable of releasing divalent cations in the presence of water. The divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may also be a bioactive glass.

Another aspect of the invention provides for a crosslinked collagen material consisting of collagen fibers, water, ions, and a glass. The material comprises from 60 wt. % to 90 wt. % of the glass.

The material comprises from 60 wt. % to 97.5 wt. % of the glass. Alternatively, the material may comprise from 65 wt. % to 90 wt. % of the glass, from 70 wt. % to 90 wt. % of the glass, from 75 wt. % to 90 wt. % of the glass, or from 80 wt. % to 90 wt. % of the glass. In any of the embodiments of this aspect, the material comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 97.5% of the glass by weight.

In some embodiments, the glass is capable of releasing divalent cations in the presence of water. The divalent and polyvalent cations include one or more of $Ca^{2+}$, $Cu^{2+}$, $Mg^{2+}$, $Fe^{2+}$, $Fe^{3+}$, $Sr^{2+}$, $Cd^{2+}$, $Al^{3+}$, $Cr^{2+}$, $Co^{2+}$, $Mn^{2+}$, $Ni^{2+}$, $Sn^{2+}$, and $Zn^{2+}$. The glass may be a bioactive glass in some embodiments of this aspect as well.

EXAMPLE 1

Preparation of Packable Graft

A "Packable graft" as defined herein is a loose collagen and 45S5 bioactive glass mixture that becomes moldable when hydrated.

The control sample "1" was prepared by hydrating 100% collagen with DI WATER (reverse osmosis deionized water prepared using the Sartorius system) until the material became moldable and then by forming a 2.5 cc sphere. The sphere was then soaked in DI WATER for 24 hours.

The test samples "2", "3", and "4" were prepared by combining 1-2 mm, 90-710 µm 45S5 bioglass, and 32-125 µm 45S5 bioglass with collagen. The dry materials were then hydrated with varying $CaCl_2$ solutions and then soaked in DI WATER for 24 hours.

Test samples "5" and "7" were prepared similarly to Samples 2-4 except HCl was used to adjust the pH of the different percent $CaCl_2$ solutions to 6.5.

Test sample "6" was prepared by replacing 5 wt % of the 32-125 µm 45S5 bioactive glass with ionomer glass, in particular ionomer glass powder TF-325. The packable graft was then hydrated and soaked in DI WATER.

The samples were evaluated on the Shimadzu Mechanical Strength Tester using compressive plates and a 1 kN Load cell. Tests were conducted under ambient conditions and all samples were tested in accordance with SOP PR-06.06 Mechanical Testing of CBG Product. The indenter displacement was set to 25 mm with a rate of 15 mm/min. The load was released when a max strength of 900 N or a max stroke of 30 mm was obtained.

The following table illustrates the composition and the compressive strength of the Packable graft samples that were evaluated.

| | Dry Composition (wt %) | | | | | Soaking | Compressive Strength |
| --- | --- | --- | --- | --- | --- | --- | --- |
| ID | Collagen | Bioglass | Misc. | Size (cc) | Hydrating Soln. | Soln. | (kPa) |
| 1 | 100 | 0 | 0 | 2.5 | RODI | RODI | 7.22424 |
| 2 | 15 | 85 | 0 | 2.5 | 0.1% $CaCl_2$ | RODI | 37.5007 |
| 3 | 15 | 85 | 0 | 2.5 | 0.25% $CaCl_2$ | RODI | 51.3565 |
| 4 | 15 | 85 | 0 | 2.5 | 1% $CaCl_2$ | RODI | 63.7604 |
| 5 | 15 | 85 | 0 | 2.5 | 0.5% $Ca(Cl)_2$ pH 6.5 | RODI | 105.645 |
| 6 | 15 | 80 | 5% Ionomer Glass | 2.5 | RODI | RODI | 128.284 |
| 7 | 15 | 85 | 0 | 2.5 | 1% $Ca(Cl)_2$ pH 6.5 | RODI | 148.51 |

The data in Table 1 indicates that after soaking, packable graft containing bioactive glass is stronger than a packable graft containing only collagen (control sample 1). The data for test samples 3-5 and 7 indicates that the increasing concentration of $Ca^{2+}$ ions in the hydration solution increases the compressive strength. Test sample 6 was prepared with the same hydrating and soaking solutions as the control (sample 1) and exhibited higher compressive strength because of the presence of the bioactive and ionomer glasses.

Samples prepared with bioglass and hydrated with various calcium chloride solutions exhibited ionic crosslinking when soaked for 24 hours in DI WATER.

EXAMPLE 2

Preparation of CBG Strips

A "CBG strip" as defined herein is collagen and 45S5 bioactive glass that is lyophilized into a rectangular shape.

The control Sample A was prepared by making a slurry with collagen and DI WATER in a 1:1 ratio by weight. The slurry was then lyophilized and subjected to DHT in molds to form 5 cc strips. The collagen strips were then soaked in DI WATER for 3 hours and lyophilized once more.

Test Sample B was prepared similarly to Sample A, except the soaking solution following DHT was 1% $Fe_2(SO_4)_3$ in place of DI WATER.

Test Samples C and E were prepared with a slurry of glass, collagen, and DI WATER adjusted to a pH of 5. Sample C contained 90 wt % glass and Sample E contained 85 wt % glass. The slurries were then lyophilized and then subjected to DHT to form strips, soaked in DI WATER for 3 hours and lyophilized once more.

Test Sample D was prepared similarly to sample E except the slurry solution was pH adjusted $CaCl_2$ in place of DI WATER and HCl and the soaking solution was PBS in place of DI WATER.

Test Sample F was prepared by combining the glass and collagen, hydrating with DI WATER, and placing the sample into the tray. The tray was then soaked in DI WATER for 3 hours and lyophilized. Sample E did not undergo DHT.

A "plate" shape was used to evaluate the strips on the Shimadzu Mechanical Strength Tester. Tests were conducted under ambient conditions and all samples were tested in accordance with SOP PR-06.06 Mechanical Testing of CBG Product. Stress was applied in a circumferential direction. Specimens were elongated at a rate of 5 mm/min until failure, with the force and extension recorded over time.

The following table illustrates the composition and the tensile strength of the CBG Strip samples that were evaluated. Sample A is the control.

| | Composition | | | | | | | | Tensile |
|---|---|---|---|---|---|---|---|---|---|
| ID | Collagen % wt | 32-125 um % wt | 710-90 um % wt | 1-2 mm % wt | Slurry Prep | Lyo | DHT | Soaking Soln. | Strength (kPa) |
| A | 100 | 0 | 0 | 0 | RODI | Twice | Once | RODI | 4.24 |
| B | 100 | 0 | 0 | 0 | RODI | Twice | Once | 1% $Fe_2(SO_4)_3$ | 7.93 |
| C | 10 | 15 | 15 | 60 | RODI + HCl | Twice | Once | RODI | 14.37 |
| D | 15 | 12.5 | 12.5 | 60 | $Ca(Cl)_2$ pH 6.5 | Twice | Once | PBS | 14.87 |
| E | 15 | 12.5 | 12.5 | 60 | RODI + HCl | Twice | Once | RODI | 26.7 |
| F | 15 | 12.5 | 12.5 | 60 | RODI | Once | None | RODI | 28.93 |

The following bulk densities were obtained for CBG strips:

Collagen Bioglass Ionically Crosslinked Composite (5 cc samples)

| | Mass (g) | Bulk Density (g/cc) |
|---|---|---|
| 1 | 3.547 | 0.7094 |
| 2 | 3.582 | 0.7164 |
| 3 | 3.915 | 0.783 |
| 4 | 3.526 | 0.7052 |
| 5 | 3.455 | 0.691 |
| 6 | 3.594 | 0.7188 |
| 7 | 3.856 | 0.7712 |
| Avg. | 3.639 | 0.7279 |
| Std. Dev. | 0.175 | 0.0350 |

% Porosity: 30-70%
Bulk Density: less than 1 g/cc

The control Sample A, was crosslinked using DHT processing. Therefore the increased tensile properties observed in the other Samples B through F can be attributed to ionic crosslinking. The tensile strength of Sample B when compared to the control indicates that ionic crosslinking occurred between the $Fe^{3+}_{(aq)}$ and the collagen fibers. Samples C and E exhibited higher tensile strengths than the control (Sample A). The compressive strength of Sample F indicates that CBG Strips can be crosslinked without DHT processing.

Samples prepared with bioglass exhibited greater tensile strength than the control that was only crosslinked with DHT. Sample F indicates that the collagen can be crosslinked and a high tensile strength can be achieved without DHT processing.

EXAMPLE 3

Preparation of CBG Composite

Materials: collagen, Bioglass® (32-125 µm, 90-710 µm, and 1-2 mm), reverse osmosis deionized water, and 2N HCl.

A slurry was prepared by mixing 0.28 g of collagen with 4.55 mL reverse osmosis deionized water and 0.49 mL 2N HCl. The slurry was mixed until all collagen was saturated. Next, all glass starting with 1-2 mm (1.68 g), then 710-90 um (0.42 g), then 32-125 um (0.42 g) was poured into the beaker labeled "slurry" and the components mixed until homogenous.

The slurry was then lyophilized in molds to form 5 cc strips. The autoclaved molds were selected based on the desired amount of slurry to be placed in the mold and as per recommendations in the Table below (e.g., 2.5 cc mold for making 2.5 cc composites).

| Size of Well | Max Amount of Slurry Per Mold |
|---|---|
| 0.5 cc | 234 cc |
| 1 cc | 350 cc |
| 2.5 cc | 240 cc |
| 5 cc | 480 cc |
| 6 cc | 240 cc |
| 8 cc | 360 cc |
| 10 cc | 480 cc |

Following the lyophilization procedure, the molds were transferred into a clean room inside of a clean bag.

Next, molds were sealed, labeled and packaged.

EXAMPLE 4

Fluid Absorption

The objective of the study was to determine the extent of fluid/blood absorption for the Bioactive Strip, MacroFORM Composite and Packable products. The study was conducted at ambient conditions: 68-74° F. and 40-60% relative humidity.

The following materials were used for the study: 5 cc Bioactive Strip, 2.5 cc MacroFORM Composite, and 5 cc MacroFORM Packable Morsels.

Dry weights were taken for each product. The devices were then hydrated with citrated sheep's blood and molded until the entirety of the product was saturated in blood. The hydrated weight was then taken of each sample and a measure of amount of blood absorbed per gram of product was calculated.

Figure 1:
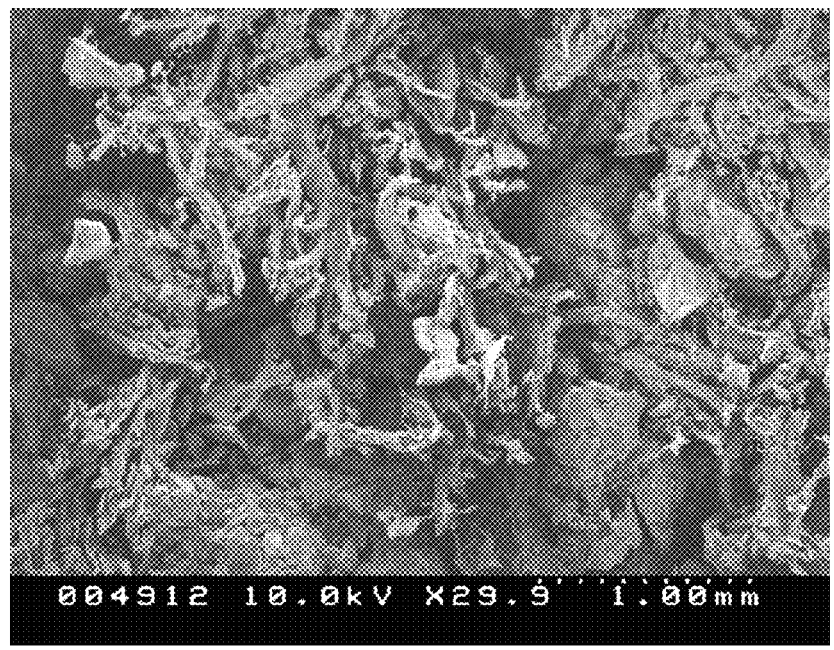
FIG. 1 is a photomicrograph of crosslinked collagen bioactive glass strip composite at 29.9× magnification.
Figure 2:
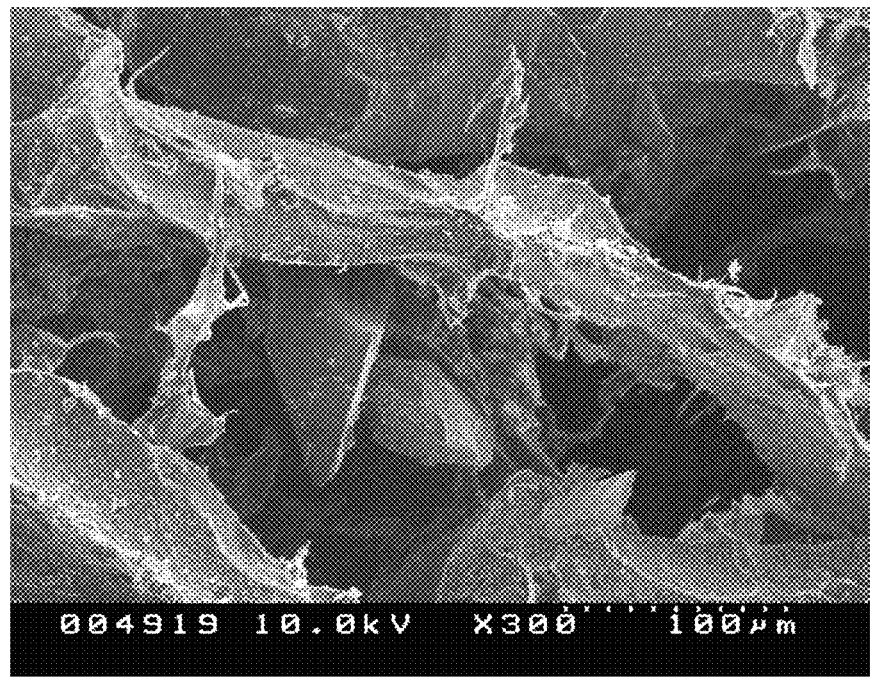
FIG. 2 is a photomicrograph of crosslinked collagen bioactive glass strip composite at 300× magnification.
Figure 3:
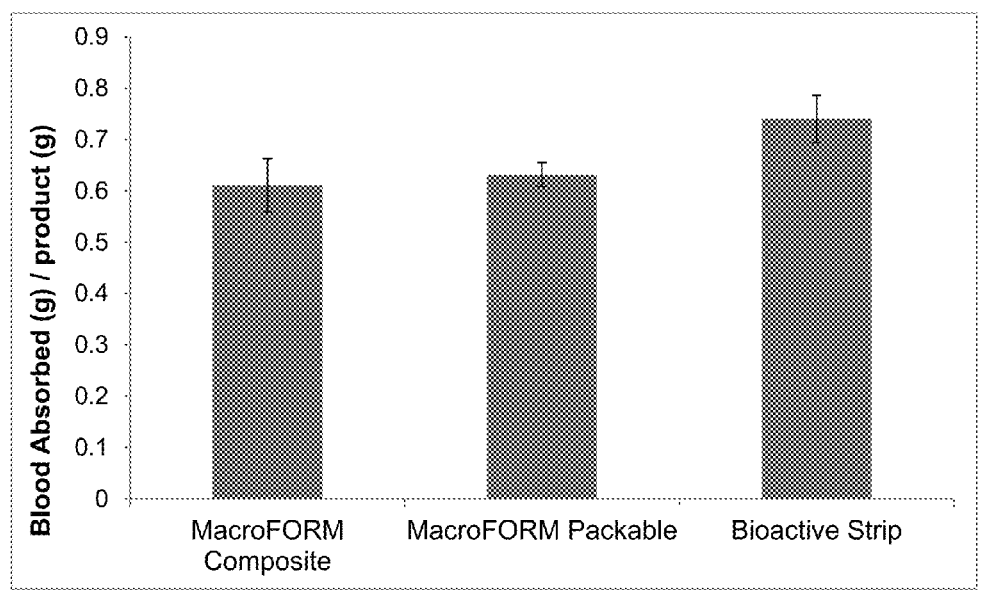
FIG. 3 depicts a graph of blood absorption of Bioactive Strip, Composite and Packable products.

The results of absorption test are show in the Table below and illustrated in FIG. 3.

TABLE

Average Blood Absorption

| SAMPLE | AVERAGE BLOOD ABSORBED PER GRAM OF PRODUCT (G) | STANDARD DEVIATION |
|---|---|---|
| 2.5 CC COMPOSITE | 0.611 | 0.052 |
| 5 CC PACKABLE GRAFT | 0.632 | 0.023 |
| 5 CC BIOACTIVE STRIP | 0.740 | 0.046 |

The MacroFORM products absorbed similar amounts of blood, approximately 0.6-0.75 grams of blood per gram of dry product.

EXAMPLE 5

Porosity Study of CBG Composite

A porosity study was conducted in order to determine the porosity of the MacroFORM Composite.

Three samples of MacroFORM Composite from 3 separate lots (sample A, sample B and sample C).

Samples were evaluated using mercury porosimetry. The process measures porosity by applying pressure to a sample immersed in mercury. The pressure required to inject mercury into the sample is inversely proportional to the size of the pores (MPS). The applicable variables were dependent (percent porosity), independent (device) and lot number), Mercury parameters were as follows: Adv. Contact Angle: 130.000 degrees; Hg Surface Tension: 485.000 dynes/cm; Rec. Contact Angle: 130.000 degrees; and Hg Density: 13.5335 g/mL.

Samples were loaded into penetrometer. The penetrometer was sealed and placed in a low pressure port. The penetrometer's cup and stem were backfilled with mercury. Excess mercury was drained.

The test was completed after the porosity of the sample was determined.

The average percent porosity for the MacroFORM Composite batches were 79.3%±2.32 for lot 1104H5, 75.9%±1.12 for lot 1104N4, and 75.3%±0.83 for lot 1104M3. The Table below lists the porosity of each lot and the average and standard deviation of the MacroFORM Composite device.

TABLE

Porosity of MacroFORM Composite Lots

| | Sample | | | | |
|---|---|---|---|---|---|
| | A | B | C | Average | Standard |
| Lot number | Porosity (%) | | | porosity (%) | deviation |
| 1104H5 | 79.5453 | 81.4333 | 76.8174 | 79.2653 | 2.3207 |
| 1104N4 | 74.9383 | 75.7577 | 77.1489 | 75.9483 | 1.1176 |
| 1104M3 | 74.3159 | 75.8637 | 75.5929 | 75.2575 | 0.8266 |

The results are illustrated in FIG. 5.

The porosity measured in these devices facilitates the absorption of water or other fluids through capillary action.

EXAMPLE 6

Porosity Study of Bioactive Strip

A study was conducted in order to determine the porosity of a Bioactive Strip. The testing was conducted by Micromeritics Pharmaceutical Services (MPS) in Norcross, Ga.

3 test samples from 3 separate lots were used in the study. Specifically, 3 NovaBone Bioactive Strip lots (1008P4, 1008P7, and 1008R1) were used. The tests protocols were developed and all testing was conducted by MPS (Norcross, Ga.).

Samples were evaluated using mercury porosimetry. The process measures porosity by applying pressure to a sample immersed in mercury. The pressure required to inject mercury into the sample is inversely proportional to the size of the pores (MPS).

Mercury Parameters included Adv. Contact Angle: 130.000 degrees; Hg Surface Tension: 485.000 dynes/cm; Rec. Contact Angle: 130.000 degrees; and Hg Density: 13.5335 g/mL.

Applicable variables included dependent (Pore Size Distribution and Percent Porosity), Independent (Device) and uncontrolled (shipping and storage conditions).

Samples were loaded into penetrometer. The penetrometer was sealed and placed in a low pressure port. The penetrometer's cup and stem were backfilled with mercury. The excess mercury was drained. The test was completed after the porosity of the sample was determined.

The Table below shows results of the porosity study of the Bioactive strips.

TABLE

Porosity of Bioactive Strip I Lots

| | Sample Number | | | | |
|---|---|---|---|---|---|
| | 1 | 2 | 3 | Average | Standard |
| Lot number | Porosity (%) | | | porosity (%) | deviation |
| 1008P4 | 63.1370 | 64.0095 | 61.8359 | 62.99 | 1.094 |
| 1008P7 | 64.1048 | 63.3744 | 64.6958 | 64.06 | 0.662 |
| 1008R1 | 61.9941 | 62.8057 | 65.4439 | 63.41 | 1.804 |

The average percent porosity for the Bioactive Strip batches were 63.0%±1.09 for 1008P4, 64.1%±0.66 for 1008P7, and 63.4%±1.80 for 1008R1. These results are illustrated in FIG. 5. There were no significant differences in percent porosity between Bioactive Strip Lots

EXAMPLE 7

Tensile Strength Study of Bioactive Strip

A tensile strength study was conducted to test the resistance of the bioactive strip to a force tending to tear it apart, measured as the maximum tension the material can withstand without tearing.

Samples of bioactive strips were hydrated and soaked in reagent grade water before testing. The samples were then placed into the grips and tested at 5 mm/min until a 50% break was detected.

The tensile stress data for bioactive strip devices in provided in the Table below.

| Sample ID | Tensile stress (kPa) |
| --- | --- |
| JC-01-94-A | 60.1595 |
| JC-01-94-A-5cc | 53.2472 |
| JC-01-94-A-5cc | 32.8249 |
| JC-01-94-A-5cc | 53.1097 |
| JC-01-94-A-5cc | 40.5517 |
| Avg | 47.9786 |
| STDEV | 11.0369167 |

The results show that the CBG material is a strong material and can withstand stress even though it is porous. In addition, the strip can bend and flex, as shown in FIGS. 6C-D.

Throughout this specification various indications have been given as preferred and alternative embodiments of the invention. However, the foregoing detailed description is to be regarded as illustrative rather than limiting and the invention is not limited to any one of the preferred embodiments. It should be understood that it is the appended claims, including all equivalents that are intended to define the spirit and scope of this invention.

The invention claimed is:

1. A combination product consisting of:
   a porous and nonporous bioactive glass, and
   collagen, and
   optionally, at least one therapeutic agent, protein, and glycosaminoglycan,
   wherein the combination product is free from calcium phosphate.

2. The combination product of claim 1, wherein the bioactive glass is present in a weight ratio of more than 80% and including and up to 97% in proportion to the total weight of the bioactive glass and the collagen.

3. The combination product of claim 1, wherein the bioactive glass is present in an amount from 85 wt. % to 97.5%.

4. The combination product of claim 1, wherein the combination product is in a form of a packable graft.

5. The combination product of claim 4, wherein the combination product consists of 75-95 wt. % bioactive glass and 5-25 wt. % collagen.

6. The combination product of claim 4, wherein the combination products consists of 85 wt. % bioactive glass and 15 wt. % collagen.

7. The combination product of claim 4, wherein the bioactive glass comprises 55-65% bioactive glass having 1000-2000 um particle size, 10-20% bioactive glass having 90-710 um particle size, and 10-20% bioactive glass having 32-125 um particle size.

8. The combination product of claim 4, wherein the bioactive glass comprises 60% bioactive glass having 1000-2000 um particle size, 12.5% bioactive glass having 90-710 um particle size, and 12.5% bioactive glass having 32-125 um particle size.

9. The combination product of claim 7, wherein the bioactive glass having the 1000-2000 um particle size is porous.

10. The combination product of claim 1, wherein the combination product is in a form of a collagen bioactive glass composite.

11. The combination product of claim 10, wherein the combination product consist of 75-95 wt. % bioactive glass and 5-25 wt. % collagen.

12. The combination product of claim 10, wherein the combination product consist of 90 wt. % bioactive glass and 10 wt. % collagen.

13. The combination product of claim 10, wherein the bioactive glass comprises 55-65% bioactive glass—having 1000-2000 um particle size, 10-20% bioactive glass having 90-710 um particle size, and 10-20% bioactive glass having 32-125 um particle size.

14. The combination product of claim 10, wherein the bioactive glass comprises 60% bioactive glass having 1000-2000 um particle size, 15% bioactive glass having 90-710 um particle size, and 15% bioactive glass having 32-125 um particle size.

15. The combination product of claim 13, wherein the bioactive glass having 1000-2000 um particle size is porous.

16. The combination product of claim 1, wherein the combination product is in a form of a strip.

17. The combination product of claim 16, wherein the combination product consist of 85-97 wt. % bioactive glass and 3-15 wt. % collagen.

18. The combination product of claim 16, wherein the combination product consist of 95 wt. % bioactive glass and 5 wt. % collagen.

19. The combination product of claim 16, wherein the combination product consist of 97.5 wt. % bioactive glass and 2.5 wt. % collagen.

20. The combination product of claim 16, wherein the bioactive glass comprises 53.5-73.5% bioactive glass having 1000-2000 um particle size, 10-20% bioactive glass having 90-710 um particle size, 10-20% bioactive glass having 32-125 um particle size.

21. The combination product of claim 16, wherein the bioactive glass comprises 63.33% bioactive glass having 1000-2000 um particle size, 15.83% bioactive glass having 90-710 um particle size, 15.83% bioactive glass having 32-125 um particle size.

22. The combination product of claim 20, wherein the bioactive glass having the 1000-2000 um particle size is porous.

23. The combination product of claim 16, wherein the bioactive glass comprises 64.68% 1000-2000 micrometer bioactive glass, 16.16% 90-710 micrometer bioactive glass, 16.16% 32-125 micrometer bioactive glass.

24. The combination product of claim 23, wherein the bioactive glass having 1000-2000 um particle size is porous.

25. A kit comprising the combination product of claim 4 and a packaging.

26. The kit of claim 25, wherein the packaging is a double peel packaging.

27. The kit of claim 25, wherein the packaging comprises
an inner tray, wherein the combination product is contained within the inner tray,
an inner tray lid,
an outer tray, wherein the inner tray is placed in the outer tray, and
an outer tray lid.

28. The kit of claim 25, further comprising a dispenser box.

29. The kit of claim 27, further comprising a syringe.

30. The kit of claim 29, wherein the combination product is disposed within the syringe.

31. The kit of claim 30, wherein the syringe comprises a removable cap.

32. The kit of claim 31, wherein the syringe is placed in the inner tray.

33. The kit of claim 25, further comprising a syringe comprising a removable cap, wherein the syringe is sealed in a pouch.

34. A kit comprising the combination product of claim 10 and a packaging.

35. The kit of claim 34, wherein the packaging is a double peel packaging.

36. The kit of claim 34, wherein the packaging comprises
an inner tray, wherein the combination product is contained within the inner tray,
an inner tray lid,
an outer tray, wherein the inner tray is placed in the outer tray, and
an outer tray lid.

37. The kit of claim 34, further comprising a dispenser box.

38. A kit comprising the combination product of claim 16 and a packaging.

39. The kit of claim 38, wherein the packaging is a double peel packaging.

40. The kit of claim 38, wherein the packaging comprises
an inner tray, wherein the combination product is contained within the inner tray,
an inner tray lid,
an outer tray, wherein the inner tray is placed in the outer tray, and
an outer tray lid.

41. The kit of claim 40, further comprising a dispenser box.

* * * * *